United States Patent [19]

Zinnes et al.

[11] 4,134,894

[45] Jan. 16, 1979

[54] PYRROLO[1,2-a]INDOLE COMPOUNDS

[75] Inventors: Harold Zinnes, Rockaway; Martin L. Schwartz, Parsippany, both of N.J.

[73] Assignee: Warner-Lambert Company, Morris Plains, N.J.

[21] Appl. No.: 902,583

[22] Filed: May 4, 1978

[51] Int. Cl.² .......................................... C07D 487/04
[52] U.S. Cl. ........................ 260/326.25; 260/326.5 B; 260/326.8; 424/274; 546/85
[58] Field of Search ................... 260/326.25, 326.5 B, 260/326.8, 326.85

[56]  References Cited
U.S. PATENT DOCUMENTS

| 3,206,470 | 9/1965 | Allen, Jr. et al. | 260/326.25 |
| 3,250,783 | 5/1966 | Remers et al. | 260/326.8 |

FOREIGN PATENT DOCUMENTS 49-18,891  2/1974  Japan ................................ 260/326.5 B

OTHER PUBLICATIONS

Franck et al., Chem. Abs., vol. 69, S1932n, (1968).
Remers et al., Chem. Abs., vol. 65, 13663b, (1966).
Laschtuvka et al., Chem. Ber., vol. 93, pp. 81–88 (1960), (Chem. Abs., vol. 54, 9882a also provided).

Primary Examiner—Raymond V. Rush
Assistant Examiner—Mary Lee
Attorney, Agent, or Firm—David B. Ehrlinger; Stephen Raines; Frank S. Chow

[57] ABSTRACT

Pyrrolo[1,2-a]indole compounds having in free base form the formulas

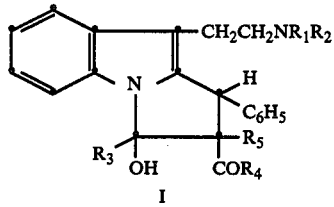

I

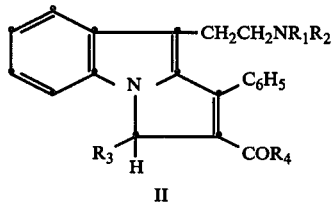

II

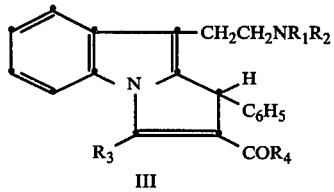

III

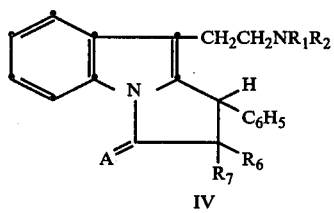

IV where $R_1$, $R_2$ and $R_3$ are lower alkyl; $R_4$ is lower alkyl, phenyl, lower alkoxy or

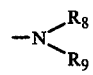

in which $R_8$ and $R_9$ are hydrogen, lower alkyl, phenyl or benzyl; $R_5$ is hydrogen or lower alkyl; A is O or NH; and $R_6$ and $R_7$ are lower alkyl, phenyl, or carbo(lower)alkoxy.

18 Claims, No Drawings

PYRROLO[1,2-A]INDOLE COMPOUNDS

SUMMARY AND DETAILED DESCRIPTION

The present invention relates to pyrrolo [1,2-a]-indole compounds having the formulas

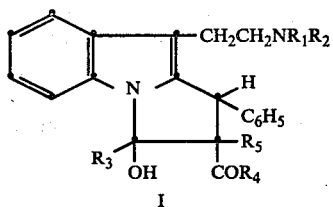

I

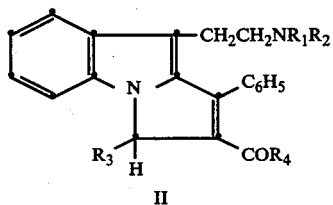

II

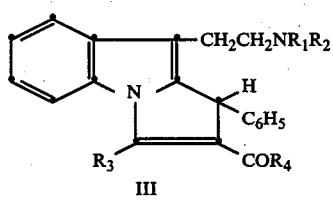

III

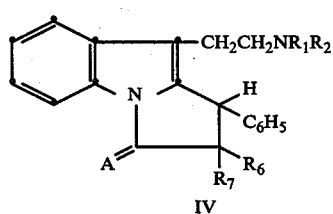

IV and acid addition salts thereof, where $R_1$, $R_2$ and $R_3$ are lower alkyl; $R_4$ is lower alkyl, phenyl, lower alkoxy or

in which $R_8$ and $R_9$ are hydrogen, lower alkyl, phenyl or benzyl; $R_5$ is hydrogen or lower alkyl; A is O or NH; and $R_6$ and $R_7$ are lower alkyl, phenyl, or carbo(lower)alkoxy. The terms "lower alkyl" and "lower alkoxy", as used herein, mean preferably 1 to 4 carbon alkyl and 1 to 4 carbon alkoxy groups.

According to one embodiment of the invention, compounds having formula I are obtained by reacting a quaternary salt having the formula

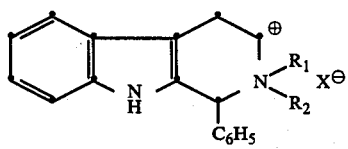

V with a β-dicarbonyl compound, $R_3COCHR_5COR_4$, in the presence of a base such as sodium hydride in a solvent which is a mixture of tetrahydrofuran (THF) with a non-hydroxylic polar solvent such as hexamethylphosphoroustriamide (HMPA), dimethylformamide (DMF), or dimethylsulfoxide (DMSO) and at temperatures ranging from 25°–100° C.; where $R_1$, $R_2$, $R_3$, $R_4$ and $R_5$ have the above-specified meaning. At these temperatures the time for completion of the initial ring opening and closure onto the indole nitrogen varies from about 3 to 48 hours.

According to another embodiment of the invention, compounds having formula II and formula III are obtained by subjecting corresponding compounds having formula I to dehydration. For this purpose, a compound having formula I suitably is reacted for 5 minutes at reflux temperature with p-toluenesulfonic acid in benzene. The resulting reaction mixture contains both of the desired corresponding dehydrated compounds having formula II and formula III and these can each be separated and isolated according to the illustrative procedures described in the examples which follow. In a preferred procedure, compounds having formula III (free of compounds having formula II) are obtained as the sole product of dehydration of compounds having formula I. This is accomplished when the reaction is carried out for 20 hours, in other words, when the reflux period is extended from 5 minutes to 20 hours.

According to still another embodiment of the invention, compounds having formula IV above are obtained by reacting a compound having formula V above in the presence of a basic catalyst with an ester or nitrile, respectively, having an acidic hydrogen in the alpha position, having the formula

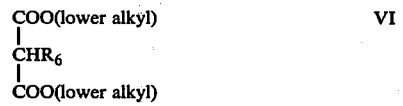

VI or the formula

VII where $R_6$ and $R_7$ have the above-specified meaning. The reaction is suitably carried out using sodium hydride as a base in a solvent which is a mixture of tetrahydrofuran with a non-hydroxylic polar solvent such as hexamethylphosphoroustriamide, dimethylformamide or dimethylsulfoxide. The reaction is suitably carried out at ambient temperatures for a period in the range from about 8 to 24 hours.

The compounds of the invention form salts with pharmaceutically acceptable acids and these salts are within the scope of the invention. These salts include, for example, salts formed with acids such as hydrochloric, hydrobromic, sulfuric, sulfonic, nitric and acetic acid and the like.

The above compounds are characterized by anti-allergy and anti-asthma properties in mammals. Thus, in a routine test conducted according to procedures described in I. Mota, Life Sciences, 7:465, 1963, and Z. Ovary, O. Bier, Proc. Soc. Exptl. Biol. Med., 81:584, 1952, the compound of formula I where $R_1$, $R_2$ and $R_3$ are methyl groups, $R_4$ is a phenyl group, and $R_5$ is hydrogen prevents allergic and asthmatic reactions in rats at dosage levels of about 25 mg./kg. intraperitoneally. In the same test and at the same dosage, the compound of formula III where $R_1$, $R_2$, $R_3$ and $R_4$ are methyl groups was found to produce 45% inhibition of the allergic response. The compounds of the invention are, therefore, indicated in the management of bronchial asthma, hay fever and other similar allergic conditions.

The compounds also exhibit anti-secretory activity. For example, the compound of formula IV where $R_1$ and $R_2$ are methyl groups, A is NH, and $R_6$ and $R_7$ are phenyl groups, when administered intraperitoneally to the Shay rat with ligated pylorus at a dose of 20 mg./kg., reduces gastric secretion by 73% and gastric acidity by 35% (Shay et al., Gastroenterology 5:43, 1945; Grossman et al., ibid. 38:343, 1960). These compounds are useful therefore as anti-secretory agents.

The compounds of the invention can be administered orally and by such compositions as tablets, pills, dispersible powders and the like. The active ingredient is mixed with at least one inert pharmaceutical diluent such as lactose and suitable granules, using agents such as water or alcohol, and the resulting granules compressed into tablets utilizing standard tableting procedures.

Liquid pharmaceutically administrable compositions are prepared by dissolving or suspending the active ingredient in a pharmaceutically acceptable carrier such as water or syrup. In addition, the compounds of this invention can be administered by inhalation therapy in which the compound is formulated by standard aerosol technique.

The compounds of this invention can be administered in dosages varying between 10-25 mg. per kg. of body weight 2 to 3 times daily. The precise dosage regimen can be varied depending on the mode of administration and the condition being treated, using procedures which are conventional in the healing arts.

The invention is illustrated by the following examples. The starting materials are commercially available exept those having formula V which are prepared as described by Hoshino et al., Ann. 516:76, 1935, and Julian et al., J.A.C.S. 57:539, 1935, which description is incorporated herewith by reference.

EXAMPLE 1.

To a slurry of sodium hydride (2.11 g., 0.05 mole, 57% mineral oil dispersion), in tetrahydrofuran (75 ml.), at 25° C., was slowly added a solution of 1-phenyl-1,3-butanedione (8.10 g., 0.05 mole) in tetrahydrofuran (75 ml.). Solid 3,4-dihydro-2,2-dimethyl-1-phenyl-1H,9H-pyrido [3,4-b]indolium iodide (20.20 g., 0.05 mole) and dimethylsulfoxide (100 ml.) were added after hydrogen evolution ceased and the brown mixture was heated on a steam bath for 18 hours. The cooled reaction mixture was poured into water (1,500 ml.). The solid product obtained was 9-[2-(dimethylamino)ethyl]-2,3-dihydro-3-hydroxy-3-methyl-1-phenyl-1H-pyrrolo[1,2-a]indol-2-yl phenylmethanone; m.p. 165°–167° C. after trituration with ether (200 ml.) and recrystallization from acetonitrile. Calculated for $C_{29}H_{30}N_2O_2$: C, 79.42; H, 6.90; N, 6.39. Found: C, 79.30; H, 6.90; N, 6.22. MW 438.6.

The corresponding hydrochloride salt is obtained by dissolving the free base in ether, treating the solution with dry hydrogen chloride until precipitation of the product is complete, and isolating the product. The hydrobromide and sulfate are obtained by treating the free base in ether solution with dry hydrogen bromide or with sulfuric acid.

EXAMPLE 2.

To a slurry of sodium hydride (0.43 g., 0.01 mole, 57% mineral oil dispersion), in tetrahydrofuran (15 ml.), at 25° C., was slowly added a solution of 2,4-pentanedione (1.0 g., 0.01 mole) in tetrahydrofuran (15 ml.). Solid 3,4-dihydro-2,2-dimethyl-1-phenyl-1H,9H-pyrido[3,4-b] indolium iodide (4.04 g., 0.01 mole) and hexamethylphosphoroustriamide (30 ml.) were added after the hydrogen evolution ceased, and the tan mixture was heated on a steam bath for 3 hours. The cooled reaction mixture was poured into water (600 ml.) and the solid product, 1-{9-[2-(dimethylamino)ethyl]-2,3-dihydro-3-hydroxy-3-methyl-1-phenyl-1H-pyrrolo[1,2-a]-indol-2-yl}-1-ethanone, recovered; m.p. 202°–204° C. with decomposition, after recrystallization from methanol (180 ml.). Calculated for $C_{24}H_{28}N_2O_2$: C, 76.56; H, 7.50; N, 7.44. Found: C, 76.64; H, 7.50; N, 7.44. M.W. 370.5.

EXAMPLE 3.

To a slurry of sodium hydride (0.43 g., 0.01 mole, 57% mineral oil dispersion) in tetrahydrofuran (15 ml.), at 25° C., was slowly added a solution of 3,5-heptanedione (1.29 g., 0.01 mole) in tetrahydrofuran (15 ml.). Solid 3,4-dihydro-2,2-dimethyl-1-phenyl-1H,9H-pyrido[3,4-b]indolium iodide (4.04 g., 0.01 mole) and hexamethylphosphoroustriamide (30 ml.) were added after the hydrogen evolution ceased and the tan mixture was heated on a steam bath for 17 hours. The cooled reaction mixture was poured into water (500 ml.) and the mixture was extracted with ethyl acetate (400 ml.). The organic layer was washed with two portions of water and with saturated sodium chloride solution, dried over sodium sulfate and evaporated. The residual product was 1-{9-[2-(dimethylamino)ethyl]-3-ethyl-2,3-dihydro-3-hydroxy-1-phenyl-1H-pyrrolo[1,2-a] indol-2-yl}-1-propanone; m.p. 147°–149° C. (dec.) after trituration with petroleum ether (100 ml.) and recrystallization from acetonitrile (18 ml.). Calculated for $C_{26}H_{32}N_2O_2$: C, 77.19; H, 7.97; N, 6.93. Found: C, 77.19; H, 8.17; N, 7.13. M.W. 404.6.

EXAMPLE 4.

To a slurry of sodium hydride (1.72 g., 0.04 mole, 57% mineral oil dispersion), in tetrahydrofuran (40 ml.), at 25° C., was slowly added a solution of 3-methyl-2,4-pentanedione (4.60 g., 0.04 mole) in tetrahydrofuran (30 ml.). Solid 3,4-dihydro-2,2-dimethyl-1-phenyl-1H,9H-pyrido[3,4-b]indolium iodide (16.16 g., 0.04 mole) and hexamethylphosphoroustriamide (100 ml.) were added after the hydrogen evolution ceased, and the tan mixture was heated on a steam bath for 17 hours. The cooled reaction mixture was poured into water (1500 ml.), and the resulting mixture was extracted with ether (1200 ml.). The organic layer was washed with two portions of water and with saturated sodium chloride solution, dried over sodium sulfate, and evaporated. The product, after trituration with petroleum ether and recrystallization from acetonitrile (160 ml.) was 1-{9-[2-(dimethylamino)ethyl]-2,3-dihydro-3-hydroxy-2,3-dimethyl-1-phenyl-1H-pyrrolo[1,2-a] indol-2-yl}ethanone; m.p. 168°–172° C. Calculated for $C_{25}H_{30}N_2O_2$: C, 76.89; H, 7.74; N, 7.17. Found: C, 77.14; H, 7.73; N, 7.22. M.W. 390.5.

EXAMPLE 5.

To a slurry of sodium hydride (4.3 g., 0.1 mole, 57% mineral oil dispersion), in tetrahydrofuran (100 ml.), at 25° C., was slowly added a solution of tertiary butyl acetoacetate (15.82 g., 0.1 mole) in tetrahydrofuran (100 ml.). Solid 3,4-dihydro-2,2-dimethyl-1-phenyl-1H,9H-pyrido[3,4-b]-indolium iodide and dimethylsulfoxide (100 ml.) were added after the hydrogen evolution ceased and the tan mixture was heated on a steam bath for 16 hours. The cooled reaction mixture was poured into water (1,500 ml.). The product after trituration with ether (100 ml.) and recrystallization from acetonitrile (350 ml.) was 1,1-dimethylethyl 9-[2-(dimethylamino)ethyl]-2,3-dihydro-3-hydroxy-3-methyl-1-phenyl-1H-pyrrolo[1,2-a]-indole-2-carboxylate; m.p. 181°–183° C. (dec.). Calculated for $C_{27}H_{34}N_2O_3$: C, 74.62; H, 7.89; N, 6.45. Found: C, 74.65; H, 7.88; N, 6.42. M.W. 434.6.

EXAMPLE 6.

To a slurry of sodium hydride (0.43 g., 0.1 mole, 57% mineral oil dispersion) in tetrahydrofuran (15 ml.), at 25° C., was slowly added a solution of 4,6-nonanedione (1.57 g., 0.01 mole) in tetrahydrofuran (15 ml.). Solid 3,4-dihydro-2,2-dimethyl-1-phenyl-1H,9H-pyrido[3,4-b]-indolium iodide (4.04 g., 0.01 mole) and hexamethylphosphoroustriamide (30 ml.) were added after the hydrogen evolution ceased, and the tan mixture was heated on a steam bath for 23 hours. The cooled reaction mixture was poured into water (400 ml.) and the resulting sticky mixture was extracted with ethyl acetate (400 ml.). The organic layer was washed with two portions of water and with saturated sodium chloride solution, dried over $Na_2SO_4$, and evaporated. The residual product was triturated with isopropyl ether (50 ml.). The resulting crystalline product was 1-{9-[2-(dimethylamino)ethyl]-2,3-dihydro-3-hydroxy-1-phenyl-3-propyl-1H-pyrrolo[1,2-a] indol-2-yl}-1-butanone; m.p. 154°–157° C. after recrystallization from acetonitrile (50 ml.). Calculated for $C_{28}H_{36}N_2O_2$: C, 77.74; H, 8.39; N, 6.48. Found: C, 77.61; H, 8.34; M. 6.30. M.W. 432.6.

EXAMPLE 7.

To a slurry of sodium hydride (0.92 g., 0.0218 mole, 57% mineral oil dispersion) in tetrahydrofuran (30 ml.) at 25° C., was slowly added a solution of 2,6-dimethyl-3,5-heptanedione (3.14 g., 0.0218 mole) in tetrahydrofuran (10 ml.). Solid 3,4-dihydro-2,2-dimethyl-1-phenyl-1H,9H-pyrido[3,4-b]-indolium iodide (8.8 g., 0.0218 mole) and hexamethylphosphoroustriamide (60 ml.) were added after the hydrogen evolution ceased, and the tan mixture was heated on a steam bath for 48 hours. The cooled reaction mixture was poured into water (1200 ml.) and the resulting sticky mixture was extracted with ethyl acetate (1800 ml.). The organic phase was washed with two portions of water and with saturated sodium chloride solution, dried over sodium sulfate, and evaporated. The residual product after trituration with isopropyl ether (50 ml.) and recrystallization from acetonitrile (20 ml.) was 1-{9-[2-(dimethylamino)ethyl]-2,3-dihydro-3-hydroxy-3-(1-methylethyl)-1-phenyl-1H-pyrrolo-[1,2-a] indol-2-yl}-2-methyl-1-propanone; m.p. 152°–154° C. Calculated for $C_{28}H_{36}N_2O_2$: C, 77.74; H, 8.39; N, 6.48. Found: C, 77.56; H, 8.31; N, 6.46. M.W. 432.6.

EXAMPLE 8.

To a slurry of sodium hydride (0.43 g., 0.01 mole, 57% mineral oil dispersion), in tetrahydrofuran (15 ml.), at 25° C., was slowly added a solution of ethyl benzoylacetate (1.92 g., 0.01 mole) in tetrahydrofuran (15 ml.). Solid 3,4-dihydro-2,2-dimethyl-1-phenyl-1H,9H-pyrido[3,4-b] indolium iodide (4.04 g., 0.01 mole) and hexamethylphosphoroustriamide (30 ml.) were added after the hydrogen evolution ceased and the tan mixture was stirred at 25° C. for 20 hours. The reaction mixture was poured into water (500 ml.) and the oily mixture was extracted with ethyl acetate (500 ml.). The organic extract was washed with two portions of water and with saturated sodium chloride solution, dried over $Na_2SO_4$, and evaporated. The residual product, after trituration with isopropyl ether (30 ml.) and recrystallization from acetonitrile (15 ml.) was ethyl 9-[2-(dimethylamino)ethyl]-2,3-dihydro-3-hydroxy-1,3-diphenyl-1H-pyrrolo[1,2-a]indole-2-carboxylate; m.p. 168°–170° C. Calculated for $C_{30}H_{32}N_2O_3$: C, 76.90; H, 6.88; N, 5.98. Found: C, 76.76; H, 7.01; N, 5.98. M.W. 468.6.

EXAMPLE 9.

To a slurry of sodium hydride (0.43 g., 0.01 mole, 57% mineral oil dispersion), in tetrahydrofuran (20 ml.), at 25° C., was slowly added a solution of N-benzylacetoacetamide (1.90 g., 0.01 mole) in tetrahydrofuran (40 ml.). Solid 3,4-dihydro-2,2-dimethyl-1-phenyl-1H,9H-pyrido[3,4-b]indolium iodide (4.04 g., 0.01 mole) and hexamethylphosphorous-triamide (30 ml.) were added after hydrogen evolution ceased and the tan mixture was heated on a steam bath for 2 hours. The cooled reaction mixture was poured into water (500 ml.) and the mixture was extracted with ethyl acetate (500 ml.). The organic phase was washed with two portions of water and with saturated aqueous sodium chloride solution, dried over $Na_2SO_4$, and evaporated. The product after trituration with acetonitrile (50 ml.) and recrystallization from acetonitrile (60 ml.) was 9-[2-(dimethylamino)ethyl]-2,3-dihydro-3-hydroxy-3-methyl-1-phenyl-N-(phenylmethyl)-1H-pyrrolo[1,2-a]indole-2-carboxamide; m.p. 211°–213° C. (dec.). Calculated for $C_{30}H_{33}N_3O_2$: C, 77.05; H, 7.11; N, 8.99. Found: C, 76.96; H, 7.27; N, 8.78. M.W. 467.6.

EXAMPLE 10.

To a slurry of sodium hydride (1.40 g., 0.033 mole, 57% mineral oil dispersion), in tetrahydrofuran (50 ml.), at 25° C., was slowly added a solution of acetoacetanilide (5.22 g., 0.03 mole) in tetrahydrofuran (25 ml.). Solid 3,4-dihydro-2,2-dimethyl-1-phenyl-1H,9H-pyrido[3,4-b]indolium iodide (12.28 g., 0.03 mole) and hexamethylphosphorous-triamide (75 ml.) were added after the hydrogen evolution ceased, and the tan mixture was heated on a steam bath for 23 hours. The cooled reaction mixture was poured into water (1200 ml.) and the resulting sticky mixture was extracted with ether (800 ml.). The organic layer was washed with two portions of water and with saturated aqueous NaCl solution, dried over $Na_2SO_4$, and evaporated. The product after trituration with petroleum ether (200 ml.) and recrystallization from acetonitrile (90 ml.) was 9-[2-(dimethylamino)ethyl]-2,3-dihydro-3-hydroxy-3-methyl-N,1-diphenyl-1H-pyrrolo[1,2-a]indole-2-carboxamide; m.p. 162°–4° C. Calculated for $C_{29}H_{31}N_3O_2$: C, 76.79; H, 6.89; N, 9.27. Found: C, 76.76; H, 7.17; N, 9.23. M.W. 453.59.

EXAMPLE 11.

A mixture of 1-{9-[2-(dimethylamino)ethyl]-2,3-dihydro-3-hydroxy-3-methyl-1-phenyl-1H-pyrrolo[1,2-a]indol-2-yl}-ethanone (13.2 g., 0.035 mole) and p-toluenesulfonic acid monohydrate (8.6 g., 0.045 mole) in benzene (500 ml.) was refluxed for 20 hours, with a water separator, and the solvent was evaporated. The residue was dissolved in methanol (150 ml.), 1N NaOH solution (100 ml.) and water (400 ml.) were added, and the mixture was extracted with ethyl acetate (600 ml.). The organic layer was washed with two portions of water and with saturated NaCl solution, dried over $Na_2SO_4$, and evaporated. The product after recrystallization from isopropyl ether (50 ml.) was 1-{9-[2-(dimethylamino)ethyl]-3-methyl-1-phenyl-1H-pyrrolo-[1,2-a]indol-2-yl}-ethanone; m.p. 100°–102° C. Calculated for $C_{24}H_{26}N_2O$: C, 80.41; H, 7.31; N, 7.82. Found: C, 80.34; H, 7.34; N, 7.90. M.W. 358.5.

The corresponding hydrochloride salt is obtained by dissolving the free base in ether, treating the solution with dry hydrogen chloride until precipitation of the product is complete, and isolating the product. The hydrobromide and sulfate are obtained by treating the free base in ether solution with dry hydrogen bromide or with sulfuric acid.

EXAMPLE 12.

a. A mixture of 9-[2-(dimethylamino)ethyl]-2,3-dihydro-3-hydroxy-3-methyl-1-phenyl-1H-pyrrolo[1,2-a]indol-2-yl phenylmethanone (12.8 g., 0.0283 mole) and p-toluenesulfonic acid monohydrate (5.9 g., 0.031 mole) in benzene (500 ml.), were refluxed for 5 minutes with a water separator and cooled to 25° C. with an ice bath. Filtration of the benzene mixture gave yellow-green solids that were dissolved in methanol (600 ml.). Water (200 ml.) was added and 1N NaOH solution also was added until pH 9 was obtained. The solid product obtained after collection and recrystallization twice from acetonitrile was {9-[2-(dimethylamino)ethyl]-3-methyl-1-phenyl-3H-pyrrolo[1,2-a]indol-2-yl}phenylmethanone; m.p. 175°–176.5° C. Calculated for $C_{29}H_{28}N_2O$: C, 82.82; H, 6.71; N, 6.66. Found: C, 82.92; H, 6.71; N, 6.70. M.W. 420.6.

b. The benzene filtrate obtained as described in paragraph a) was washed with 1N NaOH solution (50 ml.) and with two portions of water, dried over $Na_2SO_4$, and evaporated. The product after trituration with petroleum ether (100 ml.) and recrystallization from hexane (40 ml.) was {9-[2-(dimethylamino)ethyl]-3-methyl-1-phenyl-1H-pyrrolo[1,2-a]-indol-2-yl}phenylmethanone; m.p. 106°–109° C. Calculated for $C_{29}H_{28}N_2O$: C, 82.82; H, 6.71; N, 6.66. Found: C, 82.85; H, 6.55; N, 6.75. M.W. 420.6.

c. The corresponding hydrochloride salt of the free base product of paragraph (a) or paragraph (b) is obtained by dissolving the respective free base in ether, treating the solution with dry hydrogen chloride until precipitation of the product is complete, and isolating the product. The hydrobromide and sulfate are obtained by treating the free base in ether solution with dry hydrogen bromide or with sulfuric acid.

EXAMPLE 13.

A mixture of 1,1-dimethylethyl 9-[2-(dimethylamino)ethyl]-2,3-dihydro-3-hydroxy-3-methyl-1-phenyl-1H-pyrrolo[1,2-a]indole-2-carboxylate (10.8 g., 0.025 mole) and p-toluenesulfonic acid monohydrate (5.4 g., 0.028 mole) in benzene (200 ml.), was refluxed for 5 minutes with a water separator and cooled to 25° C. with an ice bath. Benzene (400 ml.) was added, and the organic layer was washed with 1N NaOH solution (100 ml.) and with two portions of water, dried over $Na_2SO_4$ and evaporated. The product after trituration with hexane (150 ml.) and recrystallization twice from acetonitrile was 1,1-dimethylethyl-9-[2-(dimethylamino)ethyl]-3-methyl-1-phenyl-3H-pyrrolo[1,2-a]indole-2-carboxylate; m.p. 131.5°–132.5° C. Calculated for $C_{27}H_{32}N_2O_2$: C, 77.85; H, 7.74; N, 6.73. Found: C, 77.70; H, 7.85; N, 6.71. M.W. 416.6.

EXAMPLE 14.

A mixture of 1-{9-[2-(dimethylamino)ethyl]-2,3-dihydro-3-hydroxy-3-methyl-1-phenyl-1H-pyrrolo[1,2-a]indol-2-yl}-ethanone (13.3 g., 0.0357 mole) and p-toluenesulfonic acid monohydrate (8.86 g., 0.0468 mole) in benzene (700 ml.), was refluxed for 2 hours with a water separator (0.9 ml., 0.05 mole of water was collected). The solvent was evaporated. The residual product after trituration with ether (200 ml.) and recrystallization from acetonitrile (80 ml.) was 1-{9-[2-(dimethylamino)ethyl]-3-methyl-1-phenyl-3H-pyrrolo[1,2-a]indol-2-yl}-ethanone tosylate salt; m.p. 201°–202° C. The mother liquor was concentrated and the residual product was dissolved in methanol (250 ml.). 1N NaOH solution and water were added to pH 9, and the product, 1-{9-[2-(dimethylamino)ethyl]-3-methyl-1-phenyl-3H-pyrrolo[1,2-a]indol-2-yl}-ethanone, was collected and recrystallized from ethyl acetate; m.p. 162°–164.5° C. Calculated for $C_{24}H_{26}N_2O$: C, 80.41; H, 7.31, N, 7.82. Found: C, 80.29; H, 7.54; N, 7.77. M.W. 358.5

EXAMPLE 15.

To a slurry of sodium hydride (2.02 g., 0.05 mole, 57% mineral oil dispersion), in tetrahydrofuran (50 ml.) at 25° C., was slowly added a solution of diethyl methyl malonate (8.7 g., 0.05 mole) in tetrahydrofuran (50 ml.). Solid 3,4-dihydro-2,2-dimethyl-1-phenyl-1H,9H-pyrido[3,4-b]indolium iodide (20.2 g., 0.05 mole) and hexamethylphosphoroustriamide (100 ml.) were added after the hydrogen evolution ceased and the tan mixture was stirred at 25° C., for 24 hours. The reaction mixture was poured into water (1,200 ml.), extracted with ether (700 ml.), and the extracts were washed with two portions of water and with saturated NaCl solution, dried over $Na_2SO_4$, and evaporated. The residual product was dissolved in ether and treated with an ether solution of hydrogen chloride gas. The product, ethyl-9-[2-(dimethylamino)ethyl]-2,3-dihydro-2-methyl-3-oxo-1-phenyl-1H-pyrrolo[1,2-a]indole-2-carboxylate hydrochloride, was collected and recrystallized from methylethyl ketone (300 ml.); m.p. 198°–200° C. (dec.). Calculated for $C_{25}H_{28}N_2O_3 \cdot HCl$: C, 68.09; H, 6.63; N, 6.35; Cl, 8.04. Found: C, 67.92; H, 6.73; N, 6.22; Cl, 8.12. M.W. 441.

The corresponding hydrobromide salt is obtained by treating an ethereal solution of the free baase with dry hydrogen bromide until precipitation of the product is complete, and isolating the product. The sulfate is obtained by treating the free base in ether with sulfuric acid.

EXAMPLE 16.

To a slurry of sodium hydride (3.37 g., 0.08 mole, 57% mineral oil dispersion), in tetrahydrofuran (100 ml.), at 25° C., was slowly added a solution of diphenylacetonitrile (15.4 g., 0.08 mole) in tetrahydrofuran (100 ml.). Solid 3,4-dihydro-2,2-dimethyl-1-phenyl-1H,9H-pyrido[3,4-b]indolium iodide (16.16 g., 0.04 mole) and hexamethylphosphoroustriamide (50 ml.) were added after hydrogen evolution ceased. The reaction mixture was stirred at 25° C. for 16 hours, poured into water (1,000 ml.) and extracted with ethyl acetate (900 ml.). The extracts were washed with two portions of water and with saturated NaCl solution, dried over $Na_2SO_4$, and evaporated. The product was 2,3-dihydro-3-imino-N,N-dimethyl-1,2,2-triphenyl-1H-pyrrolo[1,2-a]indole-9-ethanamine, after trituration with petroleum ether and recrystallization from acetonitrile (100 ml.); m.p. 154°–157° C. Calculated for $C_{33}H_{31}N_3$: C, 84.40; H, 6.65; N, 8.95. Found: C, 84.46; H, 6.74; N, 9.07. M.W. 469.6.

We claim:

1. Pyrrolo[1,2-a]indole compounds having the formulas

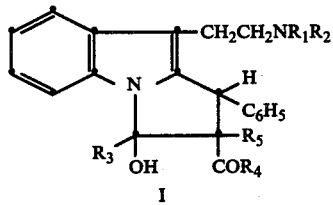
I

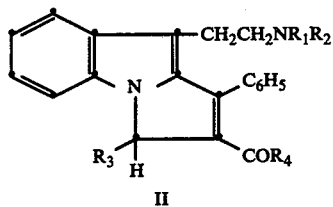
II

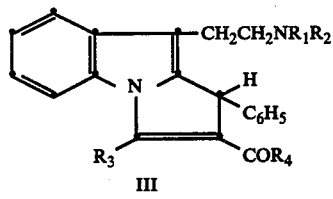
III

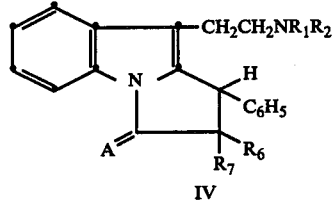
IV and pharmaceutically acceptable acid addition salts thereof, where $R_1$, $R_2$ and $R_3$ are lower alkyl;
$R_4$ is lower alkyl, phenyl, lower alkoxy or —$N(R_8)R_9$ in which $R_8$ and $R_9$ are hydrogen, lower alkyl, phenyl or benzyl;
$R_5$ is hydrogen or lower alkyl;
A is O or NH; and
$R_6$ and $R_7$ are lower alkyl, phenyl or carbo(lower)alkoxy.

2. A compound according to claim 1 which is 9-[2-(dimethylamino)ethyl]-2,3-dihydro-3-hydroxy-3-methyl-1-phenyl-1H-pyrrolo[1,2-a]indol-2yl phenylmethanone.

3. A compound according to claim 1 which is 1-{9-[2-(dimethylamino)ethyl]-2,3-dihydro-3-hydroxy-3-methyl-1-phenyl-1H-pyrrolo[1,2-a]indol-2-yl-1-ethanone.

4. A compound according to claim 1 which is 1-{9-[2-(dimethylamino)ethyl]-3-ethyl-2,3-dihydro-3-hydroxy-1-phenyl-1H-pyrrolo[1,2-a]indol-2-yl}propanone.

5. A compound according to claim 1 which is 1-{9-[2-(dimethylamino)ethyl]-2,3-dihydro-3-hydroxy-2,3-dimethyl-1-phenyl-1H-pyrrolo[1,2-a]indol-2-yl}ethanone.

6. A compound according to claim 1 which is 1,1-dimethylethyl 9-[2-(dimethylamino)ethyl]-2,3-dihydro-3-hydroxy-3-methyl-1-phenyl-1H-pyrrolo[1,2-a]indole-2-carboxylate.

7. A compound according to claim 1 which is 1-{9-[2-(dimethylamino)ethyl]-2,3-dihydro-3-hydroxy-1-phenyl-3-propyl-1H-pyrrolo[1,2-a]indol-2yl}-1-butanone.

8. A compound according to claim 1 which is 1-{9-[2-(dimethylamino)ethyl]2,3-dihydro-3-hydroxy-3-(1-methylethyl)-1-phenyl-1H-pyrrolo[1,2-a]indol-2-yl}-2-methyl-1-propanone.

9. A compound according to claim 1 which is ethyl 9-[2-(dimethylamino)ethyl]-2,3-dihydro-3-hydroxy-1,3-diphenyl-1H-pyrrolo[1,2-a]indole-2-carboxylate.

10. A compound according to claim 1 which is 9-[2-(dimethylamino)ethyl]-2,3-dihydro-3-hydroxy-3-methyl-1-phenyl-N-(phenylmethyl)-1H-pyrrolo[1,2-a]indole-2-carboxamide.

11. A compound according to claim 1 which is 9-[2-(dimethylamino)ethyl]-2,3-dihydro-3-hydroxy-3-methyl-N,1-diphenyl-1H-pyrrolo[1,2-a]indole-2-carboxamide.

12. A compound according to claim 1 which is 1-{9-[2-(dimethylamino)ethyl]-3-methyl-1-phenyl-1H-pyrrolo[1,2-a]indol-2yl}ethanone.

13. A compound according to claim 1 which is {9-[2-(dimethylamino)ethyl]-3-methyl-1-phenyl-3H-pyrrolo[1,2-a]indol-2-yl}phenylmethanone.

14. A compound according to claim 1 which is {9-[2-dimethylamino)ethyl]-3-methyl-1-phenyl-1H-pyrrolo[1,2-a]-indol-2-yl}phenylmethanone.

15. A compound according to claim 1 which is 1,1-dimethylethyl 9-[2-(dimethylamino)ethyl]-3-methyl-1-phenyl-3H-pyrrolo[1,2-a]indole-2-carboxylate.

16. A compound according to claim 1 which is 1-{9-[2-(dimethylamino)ethyl]-3-methyl-1-phenyl-3H-pyrrolo[1,2-a]indol-2yl}ethanone.

17. A compound according to claim 1 which is ethyl-9-[2-(dimethylamino)ethyl]-2,3-dihydro-2-methyl-3-oxo-1-phenyl-1H-pyrrolo[1,2-a]indole-2-carboxylate hydrochloride.

18. A compound according to claim 1 which is 2,3-dihydro-3-imino-N,N-dimethyl-1,2,2-triphenyl-1H-pyrrolo[1,2-a]indole-9-ethanamine.

* * * * *